United States Patent [19]

Wegner

[11] 4,168,201

[45] Sep. 18, 1979

[54] METHOD OF INCREASING YEAST YIELD

[75] Inventor: Eugene H. Wegner, Bartlesville, Okla.

[73] Assignee: Phillips Petroleum Co., Bartlesville, Okla.

[21] Appl. No.: 828,784

[22] Filed: Aug. 29, 1977

[51] Int. Cl.² .................... C12G 3/12; C12C 11/14
[52] U.S. Cl. .................... 435/244; 435/247; 435/930
[58] Field of Search ............ 195/49, 82, 115; 424/343

[56] References Cited

U.S. PATENT DOCUMENTS 3,844,893 10/1974 Hitzman .................... 195/115
3,878,045 4/1975 Tannahill .................... 195/49
3,879,261 4/1975 Matsumoto et al. .................... 195/49
3,929,578 12/1975 Urakami .................... 195/49
3,954,561 5/1976 Lindquist .................... 195/28 R

FOREIGN PATENT DOCUMENTS 1210770 10/1970 United Kingdom .................... 195/49

OTHER PUBLICATIONS

Snell et al., *Encyclopedia of Industrial Chemical Analysis*, vol. 4, Interscience Publishers, New York, (1967) pp. 506, 512.

*Primary Examiner*—Thomas G. Wiseman

[57] ABSTRACT

A method of increasing yield of yeast cells on a carbon source of crude methanol or crude ethanol is given.

11 Claims, No Drawings

METHOD OF INCREASING YEAST YIELD

BRIEF SUMMARY OF THE INVENTION

This invention relates to a method of increasing the yield of yeast cells which can be used as single cell protein.

BACKGROUND OF THE INVENTION

For the production of usable protein for humans and animals, experimenters are showing much interest in microorganisms which produce single cell proteins. Possible suggested foods for the microorganisms have included hydrocarbons such as petroleum and fractions thereof, e.g., natural gas, naphtha, kerosene, and fuel oil, and other carbon-containing materials such as oxygenated hydrocarbons, carbohydrates, and cellulosic substances. It is desirable to be able to feed crude, instead of refined, materials to the microorganisms in order to avoid refining costs.

Crude methanol in particular is a possible food source for certain microorganisms, as has been suggested in the literature. How to increase yeast cell growth where crude methanol or crude ethanol is the carbon source is the specific problem addressed by the present invention.

Although the prior art has suggested various possible lists of carbon sources for various lists of microorganisms, many microorganisms are very selective as to the foods which they can utilize.

The present invention has solved a problem which hitherto had not even been recognized in the prior art: i.e., 2-methyl-1-propanol is detrimental to the growth of certain yeasts which feed on crude methanol or crude ethanol.

It is an object of the present invention to increase the yield of certain yeasts on the carbon sources crude methanol and crude ethanol.

STATEMENT OF THE INVENTION

It has been discovered that in a yeast single cell protein process using as the carbon source a substrate comprising at least one alcohol selected from the group consisting of methanol and ethanol, together with a minor amount of 2-methyl-1-propanol as an impurity, and utilizing selected microorganisms which are capable of assimilating methanol or ethanol, the yield of yeast is increased by removing the 2-methyl-1-propanol from said alcohol prior to introduction of said alcohol to the fermenter.

DESCRIPTION OF THE PREFERRED EMBODIMENTS

It is believed that the best mode of removing 2-methyl-1-propanol from the carbon source for the yeasts in the process of this invention is by distillation, although other possibilities exist, such as by gas chromatographic methods and solvent extraction.

The carbon source is preferably crude methanol which contains 2-methyl-1-propanol as an impurity and which can also contain some ethanol. A less preferred but still operable feedstock is crude ethanol which contains 2-methyl-1-propanol and which could also contain some methanol.

The distillation can be readily accomplished since the boiling point of methanol is about 65° C. and the boiling point of ethanol is about 78° C., whereas that of 2-methyl-1-propanol is about 108° C. The methanol and/or ethanol distill, leaving behind the 2-methyl-1-propanol.

Distillation is done, preferably at atmospheric pressure, before the carbon source is fed to the fermenter.

Substantially all (i.e., about 98 to about 99.9 percent) of the methanol and/or ethanol can be distilled from the crude methanol and can be fed to the fermenter.

The methanol will distill at about 65° C. and the ethanol at about 78° C., if the distillation is conducted at a pressure of 1 atmosphere.

The yeasts which are most preferred are *Hansenula polymorpha*, although certain other yeasts would also be within the scope of this invention.

Yeasts which can be used in the process of this invention comprise species from the genera *Candida, Hansenula, Torulopsis, Saccharomyces, Pichia, Debaryomyces, Lipomyces, Cryptococcus, Nematospora,* and *Brettanomyces*. The preferred genera include *Candida, Hansenula, Torulopsis, Pichia,* and *Saccharomyces*.

Examples of suitable species comprise:
  *Candida boidinii*
  *Candida lipolytica*
  *Candida mycoderma*
  *Candida utilis*
  *Candida stellatoidea*
  *Candida robusta*
  *Candida claussenii*
  *Candida rugosa*
  *Candida tropicalis*
  *Candida maltosa*
  *Brettanomyces petrophilium*
  *Hansenula minuta*
  *Hansenula saturnus*
  *Hansenula californica*
  *Hansenula mrakii*
  *Hansenula silvicola*
  *Hansenula polymorpha*
  *Hansenula wickerhamii*
  *Hansenula capsulata*
  *Hansenula glucozyma*
  *Hansenula henricii*
  *Hansenula nonfermentans*
  *Hansenula philodendra*
  *Torulopsis sonorensis*
  *Torulopsis candida*
  *Torulopsis bolmii*
  *Torulopsis versatilis*
  *Torulopsis glabrata*
  *Torulopsis molishiana*
  *Torulopsis nemodendra*
  *Torulopsis nitratophila*
  *Torulopsis pinus*
  *Pichia farinosa*
  *Pichia polymorpha*
  *Pichia membranefaciens*
  *Pichia pinus*
  *Pichia pastoris*
  *Pichia trehalophila*
  *Saccharomyces cerevisiae*
  *Saccharomyces fragilis*
  *Saccharomyces rosei*
  *Saccharomyces acidifaciens*
  *Saccharomyces elegans*
  *Saccharomyces rouxii*
  *Saccharomyces lactis*
  *Saccharomyces fractum*

If desired, mixtures of two or more species of yeasts can be employed. The particular yeast employed depends in part on the carbon-containing substrate to be used. All of the yeasts listed above will grow either on methanol or ethanol, and some of them will grow on both carbon sources. However, not all will grow on both methanol and ethanol.

In the fermentation process, an aqueous mineral medium such as those known in the art to be useful for fermentations employing yeasts is supplied to the fermenter. This aqueous mineral medium provides nutrients such as nitrogen, phosphorus, magnesium, calcium, potassium, sulfur, and sodium as well as trace quantities of elements such as copper, manganese, molybdenum, zinc, iron, boron, and iodine. As is known in the art of fermentation, the concentrations and relative amounts of the nutrients can vary, depending on the yeast selected and other factors. In addition, the aqueous mineral medium preferably contains vitamins such as biotin and thiamine, as is known in the art.

Although a minor amount of the nitrogen utilized by the yeast can be provided by any ammonium salt used in preparing the aqueous mineral medium, the major amount of assimilable nitrogen is provided by the addition of anhydrous ammonia or aqueous ammonia, i.e., ammonium hydroxide, to the fermentation vessel. Although the amount of anhydrous or aqueous ammonia added will depend upon the pH desired for the fermentation mixture, generally it will be such as to maintain the fermentation mixture at a pH within the range of about 3 to about 5.

The fermentation reaction is an aerobic process wherein the oxygen needed is supplied from a free oxygen-containing gas such as air or oxygen-enriched air which is provided to maintain the contents of the fermentation vessel at a pressure which is not critical but which is generally within the range of about 0 to about 150 psig, preferably being within the range of about 0 to about 60 psig.

Although the aeration rate can vary over a considerable range, the aeration generally is conducted at a rate which is within the range of about 0.5 to about 6, preferably about 0.7 to about 4, volumes (at the pressure employed and 25° C.) of oxygen-containing gas per liquid volume in the fermenter per minute.

The fermentation temperature can vary somewhat but generally will be within the range of about 25° C. to about 65° C., preferably being within the range of about 28° C. to about 50° C.

Although the retention time of the fermentation mixture in the fermenter can vary considerably, depending in part on the fermentation temperature and yeast culture, it generally will be within the range of about 2 hours to about 20 hours, preferably being within the range of about 4 hours to about 14 hours. Preferably, the fermentation is conducted in such a manner that the alcohol substrate acts as the limiting growth factor, thereby providing good conversion of the alcohol to yeast cells.

Although the fermentation can be conducted as a batch or semi-continuous process, continuous operation is preferred. In a continuous process the alcohol substrate, the aqueous mineral medium, the ammonia, and the free oxygen-containing gas are added continuously to the fermenter. Although the volume ratio of added alcohol to added aqueous mineral medium can vary over a wide range, generally it will be within the range of about 0.5:9.5 to about 5:5, preferably being within the range of about 0.8:9.2 to about 4.5:5.5. If desired, the alcohol substrate, at least in part, and/or the ammonia, in part, can be added to the aqueous mineral medium prior to passing the aqueous mineral medium to the fermenter. Each of the streams can be introduced into the fermenter at a predetermined rate or in response to a need which can be determined by monitoring such things as concentration of alcohol substrate, pH, dissolved oxygen, oxygen or carbon dioxide in the gaseous effluent from the fermenter, and cell density. The feed rate of the various materials can be varied so as to obtain as rapid a cell growth as possible consistent with efficient utilization of the alcohol substrate, thus obtaining a high yield of yeast cells based on the alcohol charged.

The fermentation process can be conducted in any of a variety of fermentations well known in the art. For example, the fermentation can be carried out in a foam-filled fermenter or in a fermenter in which foaming is maintained at a minimum, e.g., through use of an antifoam agent.

The yeast cells can be recovered from the fermentation mixture by conventional means, e.g., by centrifugation or filtration.

The applicant conducted experiments to investigate the effect of minor amounts of selected oxygenated substances when present in methanol used in a fermentation process.

Methanol feeds of varying purity were employed in a series of continuous fermentation runs conducted at 39°–40° C. and substantially atmospheric pressure in a 4-liter fermenter with a 2-liter working volume. The yeast culture *Hansenula polymorpha* NRRL Y-11,170 was used in each run. The retention time of the fermentation mixture in the fermenter was approximately 7.3 to 8.3 hours. Oxygen was supplied by enriching air with oxygen so as to keep the dissolved oxygen in the fermentation mixture at a level above 15 percent of that which would be dissolved in the fermentation mixture saturated with air at atmospheric pressure at the fermentation temperature employed. This oxygen-enriched air was fed to the fermenter at a rate of about 1 volume (at about atmospheric pressure and about 25° C.) per volume (liquid volume in fermenter) per minute. Each carbon source in Table I was mixed with the same particular aqueous mineral medium in an amount such that the mixture of aqueous mineral medium and carbon source fed to the fermenter in each run contained about 10 volume percent methanol, except as noted in Table I (runs 7 and 8). The mixture of aqueous mineral medium and carbon source was prepared by mixing, for each liter of solution, 2 ml 85 percent $H_3PO_4$, 1 g KCl, 1.5 g $MgSO_4.7H_2O$, 0.2 g $CaCl_2.2H_2O$, 0.1 g NaCl, 5 ml of a trace mineral solution, 1 ml of a biotinthiamine hydrochloride solution, 100 ml of carbon source, about 2 drops of Mazu DF-37C antifoam agent, and sufficient deionized water to make 1 liter of solution. The trace mineral solution was prepared by mixing, for each liter of solution, 0.06 g $CuSO_4.5H_2O$, 0.08 g KI, 0.30 g $MnSO_4.H_2O$, 0.20 g $Na_2MoO_4.2H_2O$, 0.02 g $H_3BO_3$, 2.00 g $ZnSO_4.7H_2O$, 4.80 g $FeCl_3.6H_2O$, 3 ml $H_2SO_4$, and sufficient deionized water to make 1 liter of solution. The biotin-thiamine hydrochloride solution was prepared by mixing, for each 100 ml of solution, 4 mg biotin, 400 mg thiamine hydrochloride, and sufficient deionized water to make 100 ml of solution. Aqueous ammonium hydroxide (from 2 parts concentrated ammonium hydroxide and 1 part deionized water, by volume) was added to the fermenter at such a rate as to maintain the pH of the fermentation mixture within the range of 3.4 to 3.7.

In these experiments, prior operating time associated with a particular feedstock measured the time from which that particular feedstock was added to the fermenter. In each run, the rate of introduction of each feedstock was approximately constant. In each run, the retention time was about 8 hours, which was long enough for the culture to reach an essentially steady state. Because the cells consumed essentially all of the methanol and therefore grew to their maximum density by the end of their retention time of about 8 hours, it is believed that the minor differences in the input per hour of feedstock for the various runs and the differences in the number of yeast cells at the beginning of each run did not significantly influence cell yield.

The various carbon sources used, together with the corresponding prior operating time in hours, are given in Table I. The resulting cell densities in the fermenter effluent are also recorded, as well as calculated cell yields based on methanol added. To determine these cell densities and yields, the yeast cells were separated from the fermentation effluent by centrifugation, washed by suspension in water and recentrifuged, dried overnight at 100° C., and weighed.

Table I

| Run No. | Carbon Source (Prior Operating Time, hr) | Cell Density in Fermenter Effluent, g/l | Yield, g Cells per g Methanol |
| --- | --- | --- | --- |
| 1 | Methanol$^a$ (66) | 23.24 | 0.29 |
| 2 | Synthetic crude methanol$^b$ (64) | 19.23 | 0.25 |
| 3 | Methanol$^a$ (88) | 22.74 | 0.29 |
| 4 | Synthetic crude methanol, without IB$^c$ (20) | 22.54 | 0.29 |
| 5 | Methanol containing 0.3 wt. % IB$^d$ (40) | 18.44 | 0.23 |
| 6 | Methanol$^a$ (20) | 21.17 | 0.27 |
| 7 | Crude methanol$^e$ (20) | 15.20 | 0.22 |
| 8 | Ammonia-treated crude methanol$^f$ (20) | 15.19 | 0.22 |
| 9 | Methanol$^a$ (69) | 22.79 | 0.29 |

$^a$Analytical reagent grade.
$^b$Prepared by mixing with each liter of analytical reagent grade methanol 12 g dimethyl ether, 3.3 ml 2-methyl-1-propanol, 1.3 ml ethanol, 1.1 ml 1-propanol, 0.9 ml methyl formate, 1.1 ml 2-propanol, 1.0 ml methylal, and 0.024 ml of 37 weight percent formaldehyde.
$^c$Same as $^b$ except without 2-methyl-1-propanol (IB).
$^d$Prepared by mixing with each liter of analytical reagent grade methanol 3.3 ml 2-methyl-1-propanol (IB).
$^e$Crude methanol having the composition 84.20 wt. % methanol, 14.64 wt. % water, 0.01 wt. % formaldehyde, 0.02 wt. % methyl formate, 0.16 wt. % ethanol, 0.18 wt. % 1-propanol, and 0.79 wt. % 2-methyl-1-propanol. The mixture of aqueous mineral medium and crude methanol contained 8.8 vol. % methanol instead of 10 vol. %.
$^f$Prepared by admixing 100 parts by volume crude methanol as shown in $^e$ with 1.5 parts by volume concentrated ammonium hydroxide. The mixture of aqueous mineral medium and crude methanol contained 8.8 vol. % methanol instead of 10 vol. %.

The data in Table I clearly show that 2-methyl-1-propanol lowered the yield of the yeast *Hansenula polymorpha*, and conversely in the absence of the 2-methyl-1-propanol, the yield of yeast cells significantly increased.

While this invention has been described in detail for purposes of illustration, it is not to be construed as limited thereby. Rather, it is intended to cover reasonable changes and modifications which would be apparent to one skilled in the art.

What is claimed is:

1. A process for increasing the yield of yeasts on a carbon source selected from the group consisting of crude methanol containing 2-methyl-1-propanol as an impurity, crude ethanol containing 2-methyl-1-propanol as an impurity, and mixtures thereof, and said yeasts being such that they utilize as a carbon source an alcohol selected from the group consisting of methanol, ethanol, and mixtures thereof, and said yeasts being such that 2-methyl-1-propanol is detrimental to their growth, said process comprising:
   a. separating and removing 2-methyl-1-propanol from said carbon source thereby producing a purified carbon source containing methanol, ethanol or mixtures thereof; and
   b. introducing said purified carbon source to a fermenter containing a quantity of said yeasts and operating said fermenter under fermentation conditions wherein said yeasts will propagate.

2. A process according to claim 1 wherein said carbon source is crude methanol.

3. A process according to claim 2 wherein said 2-methyl-1-propanol is separated from said crude methanol by distillation.

4. A process according to claim 1 wherein said yeasts are of a genus in the group of genera comprising *Candida, Hansenula, Torulopsis, Saccharomyces, Pichia, Debaryomyces, Lipomyces, Cryptococcus, Nematospora*, and *Brettanomyces*.

5. A process according to claim 1 wherein said yeasts are of a genus in the group of genera comprising Candida, Hansenula, Torulopsis, Pichia, and Saccharomyces.

6. A process according to claim 3 wherein said yeasts are of the genus Hansenula.

7. A process according to claim 6 wherein said yeasts are of the species *Hansenula polymorpha*.

8. A process according to claim 7, wherein said fermentation is carried out at a temperature within the range from about 25° C. to about 65° C.

9. A process according to claim 7, wherein said fermentation is carried out at a temperature within the range from about 28° C. to about 50° C.

10. A process according to claim 9, wherein said fermentation is conducted as a continuous operation.

11. A process according to claim 10, wherein the volume ratio of added alcohol to added aqueous mineral medium is within the range of about 0.8:9.2 to about 4.5:5.5.

* * * * *